United States Patent [19]

Bushick et al.

[11] 3,959,337

[45] May 25, 1976

[54] AMMOXIDATION PROCESS

[75] Inventors: Ronald D. Bushick, Glen Mills; Howard P. Angstadt, Media, both of Pa.

[73] Assignee: Sun Ventures, Inc., Philadelphia, Pa.

[22] Filed: Apr. 15, 1975

[21] Appl. No.: 568,360

Related U.S. Application Data

[63] Continuation-in-part of Ser. No. 404,965, Oct. 10, 1973, abandoned, and a continuation-in-part of Ser. No. 504,938, Sept. 11, 1974, abandoned.

[52] U.S. Cl............................. 260/465 C; 252/464; 252/476
[51] Int. Cl.²..................................... C07C 120/14
[58] Field of Search ............................. 260/465 C

[56] References Cited
UNITED STATES PATENTS 3,544,617  12/1970  Oga..................................... 260/465
3,812,171  5/1974  Neikam et al. ..................... 260/465

FOREIGN PATENTS OR APPLICATIONS 41-16511  9/1966  Japan

*Primary Examiner*—Lewis Gotts
*Assistant Examiner*—Dolph H. Torrence
*Attorney, Agent, or Firm*—J. Edward Hess; Donald R. Johnson; Paul Lipsitz

[57] ABSTRACT

An ammoxidation process for preparing nitriles from m- and p-xylene whereby the formation of carbon oxides is held to a minimum which comprises reacting the xylene and ammonia at a temperature of from about 375°C. to about 500°C. and in the presence of added oxygen, the molar ratio of ammonia to xylene being about 3:1 or less, the molar ratio of oxygen to xylene being about 3:1 or less, the volume percent concentration of the feed being preferably about 3% to 10% hydrocarbon, 7% to 20% ammonia, and 10% to 20% oxygen, and the catalyst for said reaction comprising at least about 1 to 10% by weight of a vanadium bronze supported on $\alpha$-alumina.

16 Claims, No Drawings

AMMOXIDATION PROCESS

BACKGROUND OF THE INVENTION

This is a continuation-in-part of application Ser. No. 404,965 filed Oct. 10, 1973, now abandoned, and a continuation-in-part of application Ser. No. 504,938 filed Sept. 11, 1974 now also abandoned.

Ammoxidation processes are well known in the art and numerous processes with and without added oxygen and with numerous catalysts are described in various U.S. and foreign patents and publications. In those processes using added oxygen, several serious problems have hindered commercial development. One of the major problems has been the high degree of hydrocarbon burn (i.e., conversion to carbon oxides) which occurs, thus reducing conversions and wasting reactant hydrocarbon. Another related problem is ammonia burn or decomposition during the process. Because of this, generally large amounts of ammonia must be fed into the system, much of it being wasted, and this also makes necessary a large ammonia recovery system which requires a large capital investment for a commercial plant. Still another problem has been the practice of using relatively large volumes of oxygen per volume of hydrocarbon reactant and this was often accentuated by the presence of diluent gases to reduce reaction exotherms, thus making for a highly inefficient process in that large reactor and recovery equipment is also required. Reference to the disclosures in the prior art illustrate the above difficulties.

In U.S. Pat. No. 2,833,807 (Farkas et al., issued May 6, 1958 to Allied Chemical and Dye Corporation Class 260–465) it is disclosed that 3 to 30 moles of oxygen per mole of hydrocarbon and low mole ratios of ammonia to hydrocarbon (on the order of 2:1 to 3.5:1) may be used in ammoxidation reactions and the predominant nitrile product is said to be dinitrile rather than mononitrile. However, the yields of that process, as seen from the examples, are low, being on the order of 30 to 65 mole percent based on the hydrocarbon feed. The disclosure of U.S. Pat. No. 2,838,558 (Hadley et al, issued June 10, 1958, assigned to the Distillers Company, Ltd. Class 260–465) confirms these low yields in its disclosure of an ammoxidation process to form nitriles from alkyl-substituted aromatic hydrocarbons using a $V_2O_5$ catalyst supported on alumina preheated to 1000° to 1500°C., a ratio of at least 3 moles of oxygen, and about 3 to 4 moles of ammonia per mole of hydrocarbon. As can be seen from the examples of that patent, when the ammonia to xylene ratio is about 3, the yield of dinitrile is quite low, being on the order of about 30–37%. Only by increasing the ammonia to hydrocarbon ratio (on the order of about 6:1) can dinitrile yields approaching 80% be obtained (actually 77% in the disclosure) and this higher ratio, of course, leads to an inefficient process due to the need to remove the large excess of ammonia from the ammoxidation reaction products. In his U.S. Pat. No. 2,846,462 (Issued Aug. 5, 1958 and assigned to the Distillers Co., Class 260–465) Hadley further confirms this low yield of dinitriles (isophthalonitrile and terephthalonitrile) when low ammonia to hydrocarbon ratios are used. In this patent Hadley discloses that in the ammoxidation process it is preferred to use about 1.5 to 2 times the theoretical amount of ammonia for the stoichiometric reaction; i.e., about 3 to 4 moles of ammonia per mole of xylene used as the hydrocarbon, adding that the yields are generally lower when lower proportions are used. Hadley also adds that the concentration of hydrocarbon is preferably kept low, using not more than 2% by volume of the total gaseous reaction mixture. U.S. Pat. No. 3,433,823 (McMahon, issued Mar. 18, 1969 and assigned to Princeton Chemicals Research, Inc. Class 260–465.3) discloses broadly that in ammoxidation reactions of aliphatic and aromatic hydrocarbons using a specific catalyst consisting of vanadium polyphosphate admixed with another metal oxide (Mo, Cu, W, Th, U, or Zr) and which may contain added alkali metal, that low mole ratios of oxygen to hydrocarbon (0.5 to 50) and low mole ratios of ammonia to hydrocarbon (0.2 to 20) may be used. However, when illustrating the disclosed process in the examples with an aromatic hydrocarbon (p-xylene to terephthalonitrile) the oxygen to hydrocarbon ratio used is over 50:1. Furthermore, the process of the patent requires a hydrocarbon concentration of less than 3 mole percent for safety reasons, preferably 0.5 to 1.5 mole percent. Thus, a suitably efficient commercial process is precluded by the disclosure of this patent. Another prior art reference of interest is Japanese Pat. 41-16511 (Akira Ikegami, issued Sept. 19, 1966 and assigned to Mitsui Petrochemical Ind. Co., Ltd.) which discloses an ammoxidation process using as catalyst a heat-treated alumina having supported thereon vanadium oxide promoted with sodium and made by adding a sodium salt (e.g., $Na_2CO_3$) to an aqueous vanadium solution (e.g., vanadium oxalate) containing alumina and calcining the residue after evaporating to dryness. The operable range of the sodium to vanadium ratio is said to be 0.03 to 0.4 and the patent reports high yields of dinitrile when the ratio of sodium to vanadium in the catalyst is between 0.1 to 0.3, the yields dropping off significantly when outside this ratio. The broad reaction conditions disclosed for the ammoxidation inclue a reaction temperature of 300° to 600°C., preferably 350° to 500°C., an oxygen and ammonia to hydrocarbon mole ration which must be at least 4:1 to and up to 10:1, and the hydrocarbon concentration is said to be usually from 1 to 2% with respect to the reaction mixture. Thus, the process disclosed is of high reactant dilution and is likewise inefficient from a practical and commercial standpoint. Furthermore, experiments carried out under the process conditions of this Japanese Patent, have in fact, given yields of nitrile products (toluonitrile and terephthalonitrile) on the order of about 84% to 92% and not the 99% yield of terephthalonitrile reported. In addition when the process of the patent is operated at $O_2$, and $NH_3$ mole ratios of 3 to 1 moles per mole of xylene, it is found by experiment that the formation of carbon oxides (not mentioned in the patent) is rather high and the product nitriles are predominantly mono-nitriles except when the reaction feed ratio of ammonia to hydrocarbon and oxygen to hydrocarbon is very high (e.g., about 7:1). Thus, like earlier prior art, the teachings of this Japanese Patent do not lead to a process which can meet the requirements for commercial acceptance. Another recent reference also points up the need for high ammonia to hydrocarbon ratios to obtain meaningful yields of nitrile in ammoxidation reactions. G. Stefani in La-Chimica E L'Industria, 54 No. 11, Nov. 1972, pp. 984–89 states that the ammonia to hydrocarbon ratio must be on the order of 16:1 to obtain nitrile yields close to 70%.

In order to achieve an ammoxidation process which has a significant potential for commercial development the difficulties referred to above must be overcome and a combination of specific parameters must be met. Thus, the process must (a) give significant total nitrile yield; e.g., at least about 85% and preferably 90% or higher, (b) keep carbon oxides formation due to hydrocarbon burn to a minimum; e.g., preferably below about 10 to about 15% mole percent, and (c) use a minimum amount of oxygen and ammonia and employ the reactant mixture at relatively high concentration. The prior art, as pointed out above, often attempts to solve one or more of the problems, but in doing so, creates other problems which results in a process still not suitable for commercial development. Because of the complex interrelationships of the various parameters it is not possible to rationally select those conditions which, when combined, will yield an acceptable process giving product at low cost. It is quite likely that for these reasons the high volume, low cost terephthalic acid (used as a polyester fiber intermediate) is not commercially available from terephthalonitrile and subsequent hydrolysis, since no commercial plant is known for producing terephthalonitrile. In view of the need for additional sources of terephthalic acid, the development of a source of terephthalonitrile for conversion to the acid will be a significant advance in the art.

It has now been found that a commercially viable ammoxidation process meeting the above parameters and giving high yields of nitrile with low formation of carbon oxides is achieved by catalytically reacting a xylene, preferably m- or p-xylene and ammonia at a temperature of from about 375°C. to about 500°C. and in the presence of oxygen, the molar ratio of ammonia to xylene being from about 2.0 to about 3:1, the volume percent concentration of the feed being about 3% to 10% xylene, 10% to 20% ammonia and 7% to 20% oxygen, and the catalyst for said reaction comprising at least about 1% to 10% by weight of a vanadium bronze supported on α-alumina.

As indicated, the process of the invention is carried out at a temperature between about 375°C and 500°C., preferably 400°C. to 450°C, most preferably about 425°C. to 435°C. The source of oxygen is preferably air, but any oxygen source is suitable. Regardless of the oxygen source, however, the amount of oxygen must be limited and the mole ratio of oxygen to p-xylene in the reactant stream will be no more than about 3:1, preferably 2.5:1 to 3:1, although about 2.0:1 is also quite useful. Likewise the ratio of ammonia to hydrocarbon used in the process of of the invention will be about 3:1, or less, preferably 2.0:1 to 3:1. It is also to be understood that the volume percent concentration of reactants in the feed is quite high as compared to most ammoxidation procedures and the feed will comprise in percent by volume 3% to 10% p-xylene, 10% to 20% oxygen, and 7% to 25% ammonia. In the preferred method, the volume percent concentration of reactants corresponding to the above preferred ratios will comprise in percent by volume 6– 7% p-xylene, 13–18% oxygen, and 10–22 percent ammonia. The fact that the process of this invention makes possible this high concentration of reactants is significant in contributing to a very efficient overall process.

As indicated both meta- and para-xylene are useful reactants for the process. When using m-xylene to obtain isophthalonitrile, however, it is preferred to employ temperatures at the lower end of the range given above and this is in accord with art knowledge that m-xylene is more sensitive to carbon oxide formation than is the p-isomer.

It will be understood that the contact time for the reactants over the catalyst will vary over a wide range, but will usually be from about 0.1 to 20 seconds. The contact time actually used will depend upon catalyst loading, catalyst volume, temperature and other parameters and the skilled art worker will have no difficulty in selecting an appropriate contact time dependent upon these reaction parameters.

The reactant feed stread will, of course, contain other materials, as for example, the inert ingredients of air, recycled toluonitrile, and possibly some small amounts of other by-products associated with the recycle stream. This use of a recycle stream will make possible a higher yield of terephthalonitrile product.

In addition to the above required parameters of the process it is essential that a particular type of material be used as catalyst. It is known in the art that the addition of an alkali metal compound to vanadium pentoxide will, when the mixture is heated yield complex materials with anomalous valencies known as a vanadium bronzes. Such lithium bronzes are discussed by Volkov et al, Zh. Neorg. Khim: 17 (6): 1529–1532 (1972). Vanadium bronzes with sodium are described by Pouchard et al, Bull de la Soc. Chimique de France, No. 7, pages 2742–45 (1968), and No. 11 pages 4343–4348 (1967). Similarly, potassium containing vanadium bronzes are discussed by Holtzberg et al, J. Am. Chem, Soc. Vol. 78, pages 1536–40 (1956). Lithium bronzes are described by Hardy et al, Bull. de la Soc. Chimique de France, No. 4, 1056–65 (1965) and by Reisman et al Jour. Physical Chemistry 66 1181–85 (1962). Also of interest is the article by P. Hagenmuller entitled "Tungsten Bronzes", "Comprehensive Inorganic Chemistry", edited by J. C. Bailar, Jr. et al. and published in 1973 by Pergamon Press.

All of the above references as well as the references which follow are hereby incorporated herein to teach the chemistry and preparation of the bronzes which are used in this invention.

These bronze materials are prepared by mixing an appropriate alkali metal compound (e.g., carbonate, oxalate, etc.) with vanadium pentoxide and heating the mixture at an elevated temperature for several hours. Depending upon the amount of alkali metal ion added certain phases will be established in accordance with the particular phase diagram pertinent to the mixture. Thus, for example, the Holtzberg et al article referred to above describes the potassium bronze system and the sodium system is shown in the article by Slobodin et al J. Appl. Chem, (USSR) Vol. 38, pp 799–803 (April 1965). Of the above alkali metal vanadium bronzes, all of which may be used in the process of the invention, the preferred bronzes for use as catalysts are the sodium bronzes and mixtures of the various species also may be employed. Preferred species include Bronze I (BZ I) which has an atomic ratio of sodium to vanadium of 0.167, Bronze II (BZ II) where the atomic ratio is 0.417, and an alpha prime phase ($\alpha'$-phase) where the atomic ratio is 0.50. The terms Bronze I and Bronze II are used herein because these compounds correspond to the compounds called "first BRONZE" and "second BRONZE" by Slobovin and Fotiev, Jour. Applied Chemistry (USSR) 38 Vol. 4 pg. 799 April 1965 where the first bronze is characterized by having 14.3 mole percent of $Na_2O$ in its composition (as does BZ I) and the second bronze has 29.4 mole percent of $Na_2O$ (as does BZ II). These preferred Bronze I and α-phase bronzes may be further characterized by the generic empirical formula $Na_xV_2O_5$ where x is greater than zero and equal to or less than 1. Other bronze systems of the $Na_xV_2O_5$ species are known where x is greater than 1 and these are useful in the process, but are somewhat unstable and therefore not preferred. The BZ I species may be considered as $Na_2O \cdot V_2O_4 \cdot 5V_2O_5$ or $Na_{0.33}V_2O_5$ which is shown together with related members of the series at pages 573 to 575 of the Hagenmuller article as $\beta-Na_xV_2O_5$ where $x$ varies from 0.22 to 0.40, the "$\beta$" designation indicating the particular crystal phase structure of the compound. The BZ II species may be considered as $5Na_2O \cdot V_2O_4 \cdot 11V_2O_5$ or as $Na_{1+x}V_3O_8$ ($x = 0.25$) which is isotypic with $Li_{1+x}V_3O_8$ and is shown at page 584 of the Hagenmuller article mentioned above. The α-phase is characterized as $Na_xV_2O_5$ where $x = 0.7$ to 1.0 (see page 577 of the Hagenmuller article). Also characteristic of the bronzes are their x-ray diffraction patterns wherein the strongest lines are as follows:

BZ I: 9.6, 7.3, 4.75, 3.87, 3.47, 3.38, 3.21, 3.11, 3.08, 2.92, 2.90, 2.727, 2.55, 2.45, 2.38, 2.18, 1.97, 1.87, 2.803, 1.74, 1.535, 1.492.

BZ II: 6.9, 7.04, 5.81, 3.87, 3.62, 3.50, 3.45, 3.21, 3.10, 3.01, 3.67, 2.57, 2.43, 2.32, 2.27, 2.02, 1.97, 1.96, 1.81, 1.72, 1.86, 1.504, 1.333, 1.39.

$\alpha'$: 11.3, 5.645, 4.82, 4.436, 3.667, 3.456, 2.967, 2.889, 2.882, 2.799, 2.604, 2.436, 2.412, 2.291, 2.0196, 1.889, 1.803, 1.77, 1.689, 1.635, 1.592, 1.479.

The $\alpha'$-prime phase as with the other bronzes may be obtained by the methods described in the literature and placed on the support for use in the process, or it may be made in situ. This is readily achieved by treating the BZ II on the support with a reducing atmosphere (e.g., ammonia) or a stream similar to the hydrocarbon, ammonia and oxygen; e.g., an oxygen to hydrocarbon mole ratio of less than about 3.0.

As indicated the catalyst bronzes may comprise a mixture of the above discussed bronzes and preferred catalysts will comprise a mixture predominant in either BZ II or the α-prime phase or both. While BZ I used above is operable, it is preferred in order to keep the carbon oxides to a minimum to avoid having a predominant amount of BZ I in the catalyst composition.

The catalyst support used in the process of the invention will be comprised of α-alumina. α-Alumina is well known in the art and is exemplified by natural corundum and by the synthetic varieties which are commercially available. These materials have a high density (on the order of about 0.75 to 1.0 gm/cc.) and very low surface area (on the order of $6m^2/gm$ or less). Generally the α-alumina will contain enough sodium ions so that the sodium bronzes may be made without any addition of sodium or other alkali metal compounds. But if insufficient sodium is present, enough may be added to give the desired bronze. In making the supported catalyst all that is required is to make an aqueous slurry or powdered (170 mesh or finer) α-alumina, alkali metal salt (preferably carbonate) and $V_2O_5$, evaporate off the water, pelletize and calcine the pellets at about 500°–600°C. for several hours, while passing a slow flow of air through the furnace. Alternatively, and preferably, the catalyst may be placed on the support by an impregnation technique where an aqueous vanadium oxalate solution containing the appropriate amount of alkali metal is disposed onto the α-alumina support, which method is well known in the art.

As pointed out above, in making the catalyst alkali metal ions (usually in the form of the carbonate) are added to ensure that a bronze is formed. In a particularly preferred catalyst system where a sodium-vanadium bronze is desired, the amount of sodium ion employed to make the catalyst will be at a ratio of sodium to vanadium of 0.30 and such catalyst appears to be of high bronze purity devoid of extraneous materials which might degrade catalyst performance.

An indicated, the catalyst support will be comprised of α-alumina but may contain other components such as silica and other metal oxides as well as the normal contaminants found in α-alumina; e.g. iron, magnesium, and the like. However, at least about 75% by weight of the support (will be α-alumina.

The amount of catalyst on the support (e.g., catalyst loading) will be from about 1 to 20% by weight, preferably about 3 to 8%. The surface area of the catalysts used in the process is generally quite low being less than $10m^2/gm$ and usually 1 to $5m^2/gm$. Pore volume of the catalyst is such that the major proportion of the pores have diameters less than about 1 micron, being on the order of about 0.2 to 1.0 micron.

After a BZ I or a mixed BZ I and BZ II catalyst is prepared, but before its use, it is preferred to age the catalyst by a heat treatment at about 500°C. to about 750°C. for 3 to 4 hours. This treatment will convert most, if not all, of the BZ I to BZ II which is preferred over BZ I.

The ammoxidation is carried out in conventional apparatus, the reaction gases passing over the catalyst at reaction temperature and the effluent gases separated into the appropriate product and by-product streams. It will be understood that the toluonitrile by-product will be recycled to the reactor in order to increase overall yield and efficiency. In order to further describe and illustrate the invention the following examples are given:

PREPARATION OF CATALYSTS

Method A

The α-alumina support is ground into a fine powder having a particle size of about 170 mesh or less and the appropriate amount of $V_2O_5$ added to it. If analysis shows that the amount of alkali metal in the α-alumina is insufficient the desired amount sodium carbonate or other alkali metal salt is added. The mixture is then ground dry and then water is added and the mixture further agitated to make a slurry; the slurry is poured into an evaporating dish and evaporated to dryness. The dry residue is mixed further to break up agglomerates and water added to make a paste which is formed into pellets and heated at about 150°C. for about 3 hours. The pellets are then calcined at 540°C. for about 4 hours while air at the rate of 2.5 l/min is passed through the furnace. After cooling the catalyst pellets are ready for use.

Method B

Granulated alumina (8 – 16 mesh) is heated at 1300°C. for 4 hours. Vanadium pentoxide (1.25 part) is suspended in 5 parts of water, heated to 80°C., and 3.8 parts of oxalic acid are added slowly to obtain a blue-colored vanadium oxalate solution. Sodium carbonate (0.18 part) is added to this solution, and 2.5 parts of the alumina are also placed in the said solution.

The mixture is dried over a water bath, with agitation. While air is pumped in, it is indurated in a furnace at 400°C. for 16 hours to obtain the catalyst ready for use after cooling.

EXPERIMENTAL PROCEDURES

An appropriate quantity of catalyst (with or without inert diluent) was placed in a fixed bed quartz reactor (1¼ inches in diameter and 24 inches long). Inert packing above the catalyst serves as a preheater section and a small amount (about 1–2 inches) of similar inert packing was placed in the bottom of the reactor to support the catalyst in the reaction zone. The upper end of the reactor was equipped with an assembly having multiple openings through which the hydrocarbons, ammonia and air (or oxygen-helium or oxygen-nitrogen mixtures) can be metered. The reactants can be mixed in this "mixture chamber" or premixed and then fed into the reactor which is operated at essentially atmospheric pressure. The rate of gas flow was adjusted so as to produce the desired contact time at a given reaction temperature over a given volume of catalyst.

The effluent gases were passed from the reactor into a chilled flask where the products were collected along with ammonium carbonate and water. The remaining escaping gas was passed through a cold water cooled condenser, a drying tube, an ascarite tube, and finally captured in a large polyvinylchloride bag.

The analysis of the organic layer, water layer, gas sample from the bag, and the weight increase of the ascarite tube (due to $CO_2$ not bound up as ammonium carbonate) enables calculation of the results (i.e., conversion, carbon balance, yield, etc.).

Examples 1–6

Following the above details of operation catalysts were prepared and are shown in Table I. Table II shows the reaction conditions and results obtained with these catalysts in various ammoxidation runs.

Example 7

The following Table III indicates the results obtained when operating the ammoxidation process of the invention as in the above examples but with undiluted catalyst at a 5% by weight loading.

TABLE I

CATALYST IDENTIFICATION

| Cat. No. | Wt. % $V_2O_5$ on $\alpha$-$Al_2O_3$ | Alkali metal and Mole Ratio of Alkali Metal/V | Identificaton By X-Ray Diff.* | Method of Preparation | Source of $\alpha$-$Al_2O_3$ |
|---|---|---|---|---|---|
| I | 5 | Na;0.45 | BZ I:BZ II=0.25 | A | Alcoa T-71 |
| II | 8 | Na;0.507 | BZ II | A | Girdler T-1826** |
| III | 8 | Na;0.675 | BZ II | A | Girdler T-1826** |
| IV | 8 | Na;0.251 | BZ I:BZ II:1.17 | A | Alcoa T-71 |
| V | 8 | Na;0.675 | BZ II | B | Girdler T-1826** |
| VI | 8 | K;0.37 | K-V-Bronze | A | Alcoa T-71 |
| VII | 8 | Li;0.40 | Li-V-Bronze | A | Alcoa T-71 |

*When mixture is present — Intensity ratio is given.
**No alkali metal added since sufficient amount was in support.

TABLE II

AMMOXIDATION OF P-XYLENE

Reactant Concentration (Vol. %)

Temp. = 430°C.
Mole Ratio $O_2$ (air) to p-xylene = 3.1
Mole Ratio $NH_3$:p-xylene = 3:1
p-Xylene = 5.1
$NH_3$ = 15.5
$O_2$ = 15.5
$N_2$ = 63.9

| Ex. No. | Catalyst No. | Contact Time | Catalyst Bed | CO | $CO_2$ | BN* | TN+ | TPN** | TN PLUS TPN | C-Bal°. | % Conv. |
|---|---|---|---|---|---|---|---|---|---|---|---|
| 1 | III | 6 | 20 Cat: 80 Corhart | 1.2 | 8.0 | 1.1 | 48.9 | 40.9 | 89.8 | 94.4 | 62.8 |
| 2 | I | 10.2 | Undiluted | 0.7 | 7.0 | 0 | 55.7 | 36.6 | 92.3 | 106 | 48.5 |
| 3 | IV | 6.0 | 25cc. Cat: 75cc. Quartz | 1.0 | 4.9 | 0 | 63.9 | 30.2 | 94.1 | 101.5 | 38.4 |
| 4 | V | 6.0 | 50cc. Cat: 50cc. Corhart | 1.1 | 8.2 | 0 | 50.8 | 39.9 | 90.7 | 99.1 | 51.9 |
| 5 | VI | 6.0 | 25cc. Cat: 75cc. Quartz | 0.3 | 3.3 | 0 | 70 | 26.4 | 96.4 | 106.4 | 14.0 |
| 6 | VII | 6.0 | 25cc. Cat: 75cc. Corhart | 0.7 | 5.7 | 0.7 | 66.6 | 26.3 | 92.9 | 108.9 | 41.2 |

*BN=Benzonitrile
+TN=Toluonitrile
**TPN=Terephthalonitrile
°C-Bal=Carbon balance

TABLE III

AMMOXIDATION WITH 5% (LOADED) SODIUM-VANADIUM BRONZE ON α-ALUMINA

| Cat. | Temp. (°C) | C.T. (sec) | Mole Ratio $O_2$:HC | Mole Ratio $NH_3$:HC | Yield (Mole Percent) | | | | | | C-Bal. | % Conv. |
|---|---|---|---|---|---|---|---|---|---|---|---|---|
| | | | | | CO | $CO_2$ | BN | TN | TPN | TN + TPN | | |
| (a) | 430 | 6.0 | 3.0 | 3.0 | 0 | 7.1 | 0 | 55.2 | 37.7 | 92.9 | 94.0 | 63.0 |
| (b) | 435 | 6.0 | 3.0 | 3.0 | 0 | 5.1 | 0 | 62.4 | 32.5 | 94.9 | 107 | 46.1 |
| (b) | 430 | 7.3 | 3.0 | 3.0 | 0 | 5.7 | 0 | 58.0 | 36.3 | 94.3 | 95 | 59.7 |
| (b) | 430 | 7.3 | 3.0 | 3.0 | 0 | 6.1 | 0 | 57.7 | 36.2 | 93.9 | 91.4 | 56.4 |

(a) Catalyst prepared by Method A — 5% $V_2O_5$ on α-alumina $Na_2O$ content 31% (BZ II with trace of BZ I) 100 cc. cat. bed
(b) Catalyst prepared by Method B — 5% $V_2O_5$ on α-alumina $Na_2$ content 27% (BZ II) 100 cc. cat. bed

Example 8

Following the details of the above examples, an ammoxidation of p-xylene was carried out at 430°C. using a catalyst mixture of BZ II and α-prime at a catalyst loading of 8%, a mole ratio of oxygen to hdrocarbon of 2.8, an ammonia to hydrocarbon ratio of 3.0, and a contact time of 6.3 seconds. Conversion to nitrile products was 56% (Carbon Balance 96%), the yields of terephthalonitrile being 44.1%, toluonitrile being 42.6%, benzonitrile being none, carbon monoxide being 0.3% and carbon dioxide being 13%.

Example 9

Following the essential details of the above experimental techniques, an ammoxidation of p-xylene was made at 430°C. using as catalyst the α-prime phase at 8% loading which was diluted with alumina (Alcoa T-71) so that the bed was 75% by weight catalyst and 25% corundum. The oxygen (as air) to hydrocarbon mole ratio was 2.5:1, the ammonia to hydrocarbon mole ratio was 2.0:1, and contact time was 7.9 seconds. The volume amounts of the reactant feed stream was 6.6% p-xylene, 10.1% ammonia, 16.7% oxygen, the balance being essentially nitrogen. The results obtained indicated a nitrile yield of 92.5% (52.2% TPN and 40.3% TN), 0.2% benzonitrile, and 7.4% carbon oxides. Conversion was 67.9% and the carbon balance was 92.5%.

Example 10

Using the procedural details of the above examples, an ammoxidation of p-xylene was carried out at 450°C. using as a catalyst a vanadium-lithium bronze catalyst at an 8% loading both the oxygen to hydrocarbon ration and the ammonia to hydrocarbon ratio being 2:1 and contact time being 9.6 seconds. The volume amounts of the reactant feed stream were 8.5% p-xylene, 12.1% ammonia, 15.9% oxygen and the balance being nitrogen. The conversion to nitrile products was 44%, yield of terephthalonitrile being 26.7%, of toluonitrile being 65.8%, of benzonitrile 0.1%, and carbon oxide formation was 7.4%. Carbon balance was 101%.

Example 11

An ammoxidation of p-xylene was carried out as above using a non-diluted catalyst bed of an 8% BZ II catalyst at 400°C., a mole ratio of oxygen to hydrocarbon of 2.7:1 and of ammonia to hydrocarbon of 2.7:1, a contact time of 6 seconds and the volume concentration of the reaction stream being 6% p-xylene, 16% oxygen, 16% ammonia, and 62% nitrogen. Conversion of the p-xylene was 57% per pass yielding 47% TPN, 42% TN, and 11% carbon oxides.

Example 12

Using m-xylene at 390°C., but under the other reaction conditions of Example 11, gives isophthalonitrile instead of terephthalonitrile with similar conversion and yield.

Example 13

Although the above examples illustrate the process of the invention with a fixed bed system, it will be understood that the process is equally useful with other systems such as a fluidized bed, a moving bed, and the like. Thus, for example, a suitably high yield of total nitriles (e.g., toluonitrile and terephthalonitrile) is obtained from p-xylene with a fluidized bed system using a stainless steel tube 1.25 inches in diameter and 6 feet long operating under the following parameters:

| | |
|---|---|
| Catalyst: | Bronze II on α-alumina<br>800 g. catalyst in tube<br>Expanded bed height 2' to 4' |
| Reaction Conditions: | 400°C.<br>$O_2$/p-xylene = 2.5<br>$NH_3$/p-xylene = 2.5<br>Contact time = 6 sec.<br>Pressure = 1 atmosphere |

Example 14

In another fluidized bed run using a Bronze II catalyst made with a ratio of sodium to vanadium of 0.30, excellent results were obtained as shown in the following Table IV:

| Operating Conditions |
|---|
| Temperature: 385°C.<br>$O_2$:p-xylene mole ratio:2.5<br>$NH_3$:p-xylene mole ratio:3.0<br>Contact Time: 6 seconds<br>Pressure: 3 psig. |
| Single-Pass Results Obtained |

| | |
|---|---|
| p-xylene Conversion: | 59% |
| TN plus TPN: | 87% |
| TPN/TN Mole Ratio: | 1.29 |
| Ammonia burn: | 13% (of $NH_3$ fed) |

When carrying out the process in a fixed bed mode the pressure of the system will be preferably essentially atmospheric as conversions and selectivity in the conventional fixed bed drops off at higher pressures due to hot spotting. To avoid such problems it is preferable to employ a fluidized bed system which overcomes the hot spotting and lends itself to very efficient operation at higher pressures. Fluidized bed operations will be carried out preferably at from about 1 to about 5 atmospheres.

The invention claimed is:

1. An ammoxidation process for preparing nitriles from m- and p-xylene which comprises reacting said xylene and ammonia at a temperature of from about 375°C. to about 500°C. and in the presence of added oxygen, the molar ratio of ammonia to xylene being no more than about 3:1, the molar ratio of oxygen to xylene being no more than about 3:1, the volume percent concentration of the reactant feed being about 3% to 10% xylene, 7% to 25% ammonia, and 10% to 20% oxygen, and the catalyst for said reaction comprising at least about 1 to 10% by weight of an alkali metal vanadium bronze supported on $\alpha$-alumina.

2. An ammoxidation process for preparing terephthalonitrile from p-xylene which comprises reacting p-xylene and ammonia at a temperature of from about 400°C. to about 450°C. and in the presence of added oxygen, the molar ratio of oxygen to xylene being from about 2:1 to about 3:1, the volume percent concentration of the reactant feed being about 3% to 10% xylene, 7% to 25% ammonia and 10% to 20% oxygen, and the catalyst for said reaction consisting essentially of at least about 1 to 10% by weight of an alkali metal vanadium bronze supported on $\alpha$-alumina.

3. The process of claim 2 wherein the catalyst is a sodium vanadium bronze.

4. The process of claim 3 where the catalyst is predominantly BZ II or the $\alpha$-prime phase.

5. The process of claim 2 where the temperature is from about 400°C. to about 435°C., the ratio of oxygen to xylene and of ammonia to xylene is from about 2.0:1 to about 3.0:1, the concentration of feed is about 6% to about 7% xylene, about 10% to about 22% ammonia and about 13% to about 18% oxygen.

6. The process of claim 5 where the catalyst is predominantly BZ II.

7. The process of claim 5 where the catalyst is predominantly the $\alpha$-prime phase.

8. The process of claim 5 where the catalyst is a mixture of BZ II and the $\alpha$-prime phase.

9. The process of claim 1 where the xylene is m-xylene and the reaction temperature is from about 375°C. to about 400°C.

10. The process of claim 3 where the catalyst pore diameter is from about 0.2 to about 1 micron.

11. The process of claim 2 where the process is carried out in a fixed bed.

12. The process of claim 2 where the process is carried out in a fluidized bed.

13. The process of claim 5 carried out in a fluidized bed.

14. The process of claim 5 carried out in a fixed bed.

15. The process of claim 4 carried out at essentially atmospheric pressure and in a fixed bed mode.

16. The process of claim 4 carried out at a pressure of from about 1 to about 5 atmospheres and in a fluidized bed.

* * * * *